United States Patent
Bhatnagar et al.

(10) Patent No.: US 9,707,261 B2
(45) Date of Patent: Jul. 18, 2017

(54) **ANTI DENGUE ACTIVITY OF *CISSAMPELOS PAREIRA* EXTRACTS**

(75) Inventors: Pradip Kumar Bhatnagar, Exton, PA (US); Chandra Kant Katiyar, Gurgaon (IN); Navin Khanna, New Delhi (IN); Dilip Jatashankar Upadhyay, Thane (IN); Sathyamangalam Swaminathan, K. V. Rangareddy (IN); Kona Srinivas, East Godavari (IN); Navin Sharma, North West Delhi (IN); Anil Kanaujia, Kanpur Nagar (IN); Ruchi Sood, New Delhi (IN); Smita Singhal, Ghaziabad (IN); Gyanesh Shukla, Jalaun (IN); Rajeev Duggar, Jodhpur (IN); Pawan Kumar Pareek, Bikaner (IN); Yogendra Singh, Kanpur Nagar (IN); Seema Khan, New Delhi (IN); Rajendra Raut, Buldana (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 1236 days.

(21) Appl. No.: 13/145,732

(22) PCT Filed: Jan. 23, 2010

(86) PCT No.: PCT/IB2010/050299
§ 371 (c)(1),
(2), (4) Date: Jan. 10, 2012

(87) PCT Pub. No.: WO2010/084477
PCT Pub. Date: Jul. 29, 2010

(65) Prior Publication Data
US 2012/0107424 A1    May 3, 2012

(30) Foreign Application Priority Data
Jan. 23, 2009 (IN) .............. 141/DEL/2009

(51) Int. Cl.
*A61K 36/59* (2006.01)
(52) U.S. Cl.
CPC .................. *A61K 36/59* (2013.01)
(58) Field of Classification Search
None
See application file for complete search history.

(56) References Cited

FOREIGN PATENT DOCUMENTS

JP    2006-137690    6/2006    ........... A61K 36/18

OTHER PUBLICATIONS

Ramirez et al. Cissampeloflavone, a chalcone-flavone dimer from Cissampelos parerira, 2003 Phytochemistry, 64: 645-647.*
Bhcrata Bhaiaja Ratnckara ('BBR'), compiled by Nagnadcsa Chaganlcla ha, Translated by Gopinath Gupta, vol. III, B. Jain Publishers, New Delhi, 2nd Exition, Reprint Aug. 1999—first published from 1000 BC.*
Amoruso, Michelle: Re-emerging infectious disease and ethnic stratification: Dengue fever in Trinidad and Tobago; Southern Methodist University, ProQuest, UMI Dissertations Publishing, 2007, 253 pages.*
Barrett, "Current Status of Flavivirus Vaccines", *Annals of the New York Academy of Sciences*, 951:262-271 (2001).
Gubler, "Dengue and Dengue Hemorrhagic Fever", *Clinical Microbiology Reviews*, 11(3):480-496 (1998).
Hussein et al., "Inhibitory Effects of Sudanese Medicinal Plant Extracts on Hepatitis C Virus (HCV) Protease", *Phytotherapy Research*, 14(7):510-516 (2000).
Reddy et al., "A new BIS-Andrographolide Ether from *Andrographis paniculala* Nees and evaluation of anti-HIV activity", *Natural Product Research*, 19(3):223-230 (2005).
Hattori et al., "Inhibitory Effects of Various Ayurvedic and Panamanian Medicinal Plants on the Infection of Herpes Simpiex Virus-1 in vitro and in vivo", *Phytotherepy Research*, 9:270-276 (1995).
Chung et al., "Investigation of Korean Plant Extracts for Potential Phytotherapeutic Agents Against B-Virus Hepatitis", *Phytotherapy Research*, 9(6):429-434 (1995).
Parida et al., "Inhibitory potential of neem (*Azadirachta indica* Juss) leaves on Dengue virus type-2 replication", *Journal of Ethnopharmacology*, 79:273-278 (2002).
Pompei et al., "Glycyrrhizic acid inhibits virus growth and inactivates virus particles", *Nature*, 281(5733):689-690 (1979).
Chiang et al., "Antiviral activities of extracts and selected pure constituents of *Ocimum basilicum*", *Chemical and Experimental Pharmacology and Physiology*, 32:811-816 (2005).
Yeh et al., "Effect of an extract from *Phyllanthus amarus* on hepatitis B surface antigen gene expression in human hepatoma cells", *Antiviral Research*, 20:185-192 (1993).
Thyagarajan et al., "Effect of Phyllanthus Amarus on Chronic Carriers of Hepatitis B Virus", *The Lancet*, 332(8614):764-766 (1988).
Kurokawa et al., "Efficacy of traditional herbal medicines in combination with acyclovir against herpes simplex virus type 1 infection in vitro and in vivo", *Antiviral Research*, 27:19-37 (1996).
Kucera and Herrmann, Jr., "Antiviral Substances in Plants of the Mint Family (*Labiatae*). I Tannin of *Melissa officinalis*", *Proceedings of the Society for Experimental Biology and Medicine*, 865-869 (1966).
Herrmann, Jr. and Kucera, "Antiviral Substances in Plants of the Mint Family (*Labiatae*). II. Nontannin Polyphenol of *Melissa officinalis*", *Proceedings of the Society for Experimental Biology and Medicine*, 869-874 (1966).
Aswal et al., "Screening of Indian plants for biological activity: Part XV", *Indian Journal of Experimential Biology*, 34: 444-467 (1996).

(Continued)

*Primary Examiner* — Terry A McKelvey
*Assistant Examiner* — Catheryne Chen

(57) ABSTRACT

The present invention relates to the anti dengue activity of the *cissampelos pareira* extracts. Pharmaceutical compositions comprising extracts of *cissampelos pareira* and processes for the preparation of extracts of *cissampelos pareira* are also provided.

2 Claims, 2 Drawing Sheets

(56) References Cited

OTHER PUBLICATIONS

Khanam et al., "Induction of Neutralizing Antibodies Specific to Dengue Virus Serotypes 2 and 4 by a Bivalent Antigen Composed of Linked Envelope Domains III of These Two Serotypes", *The American Journal of Tropical Medicine & Hygiene*, 74(2):266-277 (2006).

Markland et al., "Broad-Spectrum Antiviral Activity of the IMP Dehydrogenase Inhibitor VX-497: a Comparison with Ribavirin and Demonstration of Antiviral Additivity with Alpha Interferon", *Antimicrobial Agents and Chemotherapy*, 44(4):859-866 (2000).

Puig-Basagoiti et al., "Triaryl Pyrazoline Compound Inhibits Flavivirus RNA Replication", *Antimicrobial Agents and Chemotherapy*, 50(4):1320-1329 (2006).

*Ayurvedic Pharmacopoeia of India*. First Edition, Part 1, vol. 1 (1989), New Delhi: Govt of India—Ministry of Health and Family Welfare, Dept of Indian System of Medicine and Homoeopathy. pp. 92-93.

*The Wealth of India: A Dictionary of Indian Raw Materials and Industrial Products, Raw Materials*, vol. II (1985). Delhi:Council of Scientific and Industrial Research, pp. 183-184.

*Database on Medicinal Plants Used in Ayurveda*. vol. 2, New Delhi:Central Council for Research in Ayurveda and Siddha, Dept of Indian System of Medicine and Homoeopathy, pp. 438-450.

Badilla et al., "Effects of an extract of Cissampelos pareira on the hemorrhagic and proteolytic activities from Bothrops asper venom", *Medicinal & Aromatic Plants Abstracts*, 30(4) (2008) abstract only (Abstract of article from *Pharmacognosy Magazine*, 4(13)27-31 (2008)).

Amresh et al., "Antinociceptive and antiarthritic activity of Cissampelos pareira roots", *Medicinal & Aromatic Plants Abstracts*, 30(1) (2008) abstract only (Abstract of article from *Journal of Ethnopharmacology*, 111(3):531-536 (2007)).

Ganguly et al., "Antifertility activity of the methanolic leaf extract of Cissampelos pareira in female albino mice", *Medicinal Aromatic Plants Abstracts*, 30(1) (2008) abstract only (Abstract of article from *Journal of Ethnopharmacology* 111(3):688-691 (2007)).

Hullatti and Sharada, "Comparative antipyretic activity of Patha: An Ayurvedic drug", *Medicinal Aromatic Plants Abstracts*, 30(1) (2008) abstract only (Abstract of article from *Pharmacognosy Magazine*, 3(11):173-176 (2007)).

Jiang et al., "Traditional Medicine in Kenya, India and etc.", *Foreign Medical Science—The Part of Chinese Traditional Medicine*, 25(1):61-64 (2003) (English translation included).

\* cited by examiner

ANTI DENGUE ACTIVITY OF CISSAMPELOS PAREIRA EXTRACTS

FIELD OF THE INVENTION

The present invention relates to the anti dengue activity of *cissampelos pareira* extracts. Pharmaceutical compositions comprising extracts of *cissampelos pareira* and processes for the preparation of extracts of *cissampelos pareira* are also provided.

BACKGROUND OF THE INVENTION

Dengue viruses (DEN1-4), mosquito-borne members of the family Flaviviridae, are human pathogens of global significance. Of the 1 million annual cases of dengue haemorrhagic fever/dengue shock syndrome, about 2-5% are fatal. Currently, there is no vaccine or antiviral drug to treat DEN infections (Ann, N.Y. Acad. Sci., 951, p. 262-271 (2001), and Clinical Microbiology Reviews, July, p. 480-496 (1998)).

Herbal medicines have emerged as a unique approach for meeting the need for safe, effective and relatively inexpensive new remedies for a variety of disorders. These represent the fastest growing segment among all of alternative medicine. The herbal medicines are produced in different forms, which range from crude, decocted herbs to refined, concentrated and standardized extracts. The health benefit from taking those herbals also varies with the quality of the products and the knowledge of consumers on the products. Some of the products have to be used under a physician's supervision, particularly those indicated for serious diseases although the majority of herbal medicines are generally safe.

Many plants have been scientifically evaluated on experimental models as antiviral agents viz. *Acacia nilotica* for inhibitory effects on Hepatitis C virus protease (Hussein et. al., Phytotherapy, Res., 14(7) p. 510-16 (2000)), *Andrographis paniculata* for HIV-1 inhibitory activity (Reddy et. al., Nat. Prod. Res., 19(3): p. 223-30, (2005)), *Areca catechu* for inhibitory activity on the plaque formation of Herpes simplex virus type-1 (Hattori et. al., Phytotherapy Res., 9, p. 270-276 (1995)), and also for inhibition of Hepatitis B virus DNA polymerase (Chung et. al., Phytotherapy Res, 9, p. 429-434 (1995)), *Azadirachta indica* for inhibition of replication of Dengue virus type 2 (Parida et. al., J. Ethnopharmacol., 79, p. 273-78 (2002)), *Glycyrrhiza glabra* for inhibition of growth and cytopathology of several unrelated DNA and RNA viruses and also for inactivating herpes simplex virus irreversibly (Pompei et. al., Nature, 281 (5733): p. 689-90 (1979)), *Ocimum basilicum* for inhibition of DNA viruses viz. herpes virus (HSV); adenovirus (ADV); Hepatitis B and also inhibition of RNA viruses viz. coxsackie virus B1 (CVB1), enterovirus 71 (EV 71) (Chiang et. al., Clin. Exp. Pharm. Physiol., 32, p. 811-16 (2005)), *Phyllanthus amarus* for suppression of Hepatitis B surface antigen (HBsAg) gene expression in human hepatoma cells (Yeh et. al., Antiviral Res., 20, p. 185-92 (1993)), and for HBsAg clearance (Thyagarajan et. al., Lancet, p. 764-66 (1988)), and *Terminalia chebula* against herpes simplex virus type 1 infection (Kurokawa et. al., Antiviral Res., 27, p. 19-37 (1995)). Further, antiviral agents of plant origin, being non-toxic and inexpensive, can have easy acceptability (Parida et al, J. Ethnopharmacol., 79, p. 273-278 (2002)).

Though the association of several herbal extracts with antiviral activity is well documented, however, a systematic search for anti-DEN virus activity in plant extracts has not been undertaken so far. It was earlier elucidated that extracts from different parts of plants may yield a source for antiviral compounds (Herrmann et. al., Proc. Soc. Exp. Biol. Med., 124, p. 865-74 (1967)). This prompted several workers to undertake a concerted search for antiviral compounds of plant origin that in turn culminated in a report which showed that a number of plants exhibited efficacy to suppress the growth of several viruses (Aswal et. al., Ind. J. Exp. Biol., 34, p. 444-67 (1996)).

*Cissampelos pareira* Linn (Family: Menispermaceae, English Name: Velvet Leaf, Hindi Name: Patha, Sanskrit Name: Ambasthaki) is a climbing shrub distributed throughout the warm parts of Asia, East Africa and America and common in India and Ceylon. It is common in warm and dry regions of tropical and sub-tropical parts of India up to an altitude of about 1500 m. It is found in Himachal Pradesh, Chota Nagpur, Bihar, West Bengal, Punjab, Rajasthan particularly in the east of Aravalli, hilly forests of Marathwada, Konkan, Deccan, Bababuden hills of Mysore, Tamil Nadu (*Ayurvedic Pharmacopoeia of India*, First Edition, Part 1, Vol 1, p. 92-93; Govt of India, Ministry of Health and Family Welfare, Dept of Indian System of Medicine and Homoeopathy, New Delhi; *The Wealth of India, A Dictionary of Indian Raw Materials and Industrial Products, Raw Materials*, Vol II, Council of Scientific and Industrial Research, Delhi; *Database on Medicinal Plants Used In Ayurveda*, Vol 2, Central Council for Research in Ayurveda and Siddha, Dept of Indian System of Medicine and Homoeopathy, New Delhi).

*Cissampelos pareira* Linn is an Ayurvedic medicinal plant used traditionally for the treatment of a number of diseases. It is said to be bitter, astringent, anthelmintic, carminative, stomachic, digestive, anti-inflammatory, diuretic, febrifuge, expectorant, galactogogue and bitter tonic. It is useful in dyspepsia, abdominal pain, diarrhoea, dysentery, fever, cough, coryza, asthma and lactation disorders (*Database on Medicinal Plants Used In Ayurveda*, Vol 2, Central Council for Research in Ayurveda and Siddha, Dept of Indian System of Medicine and Homoeopathy, New Delhi).

Dengue fever is not mentioned as such in the Ayurvedic classical textbooks; however, many types of "Jwara" have been enumerated in these textbooks along with their signs and symptoms. It is often difficult to correlate one type of "Jwara" as a clinical counter-part of a particular type of "fever" mentioned in the contemporary science. In classical Ayurvedic textbooks, some of the signs and symptoms of Dengue fever do correlate with a type of fever referred to as viz. "Vata-Pittaja Jwara". The plants which have been mentioned to be used in a condition known as "Vata-Pittaja Jwara", "Vataj Jwara" and "Pittaj Jwara" in the classical textbooks of Ayurveda were selected and their Ayurvedic attributes were studied which basically falls under the headings viz. "Rasa"; "Guna"; "Veerya"; "Vipaaka"; and "Dosha-Karma". All these attributes were thoroughly studied for each and every plant and a hypothesis was developed wherein it was postulated that any herb which at least possess viz. Tikta and/or Kashaya Rasa, Laghu and/or Tikshna Guna, Ushna or Sheeta Veerya, having Katu Vipaaka and Vata and/or Pitta Shaamaka would be useful in alleviating signs and symptoms correlating with Dengue fever. Some of the attributes viz. Katu Rasa and Ruksha Guna were in addition to the attributes which were proposed in the hypothesis. Therefore, on the basis of the proposed hypotheses and the presence of proposed, as well as, additional Ayurvedic attributes thereupon, *cissampelos pareira*

*Linn* (Ambasthaki/Patha) was selected to be undertaken for studying its therapeutic effect in Dengue Fever.

SUMMARY OF THE INVENTION

In one aspect of the invention, there are provided extracts of *cissampelos pareira*.

In another aspect of the invention, a pharmaceutical composition comprising an extract of *cissampelos pareira* along with one or more of pharmaceutically acceptable carriers, excipients or diluents is provided.

In another aspect of the invention, a process for the preparation of extracts of *cissampelos pareira* is provided.

In another aspect of the invention, there is provided a method of treating dengue virus infection.

The details of one or more embodiments of the invention are set forth in the description below. Other features, objects and advantages of the invention will be apparent from the description.

DETAILED DESCRIPTION OF THE INVENTION

Figure 1:
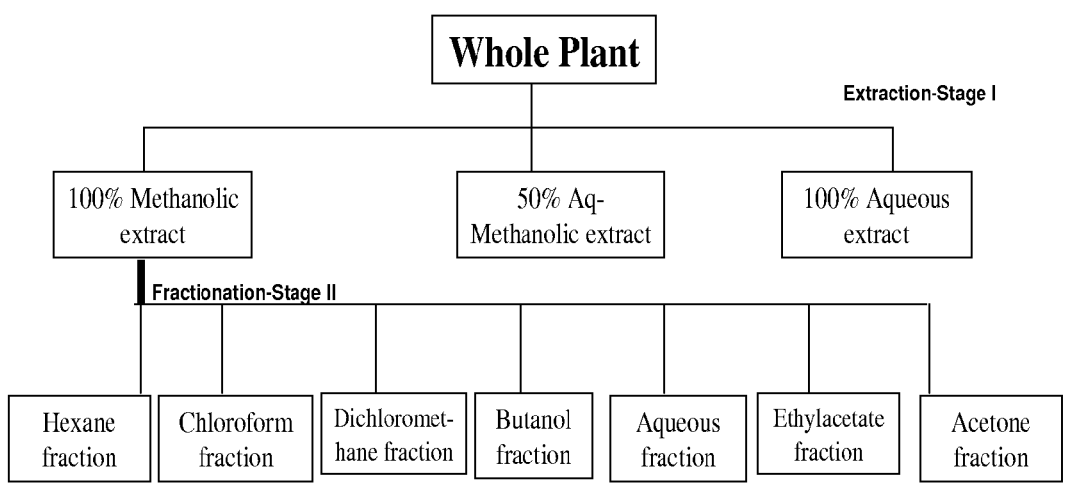
FIG. 1 shows flow diagram for the bioassay guided fractionation process.
Figure 2:
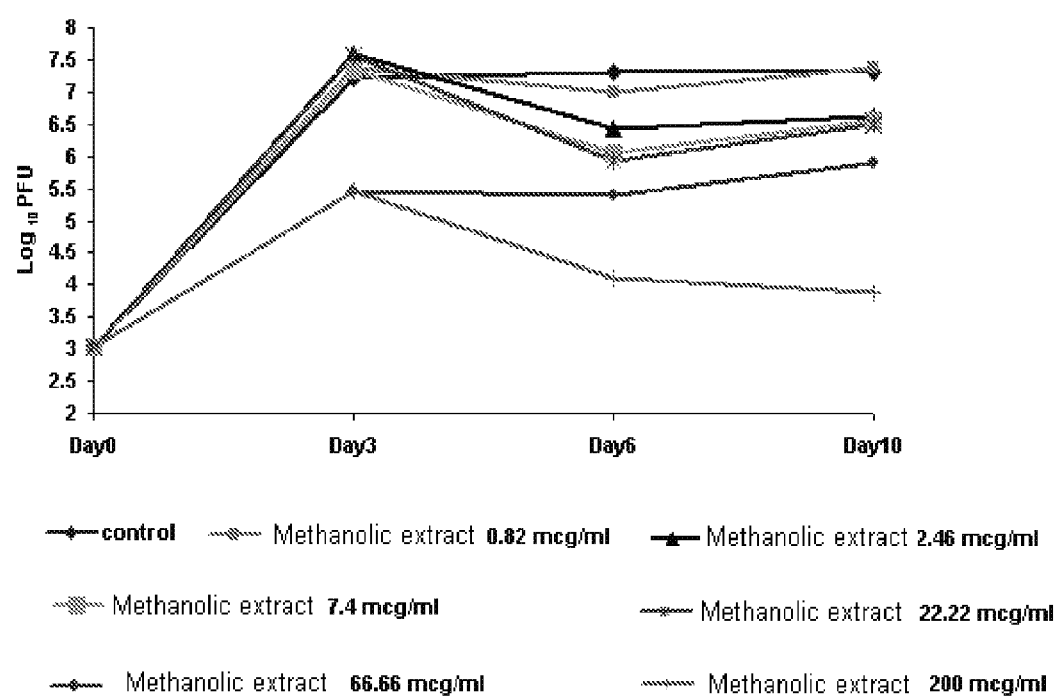
FIG. 2 shows anti-dengue activity of methanolic extract of *c. pareira* against Dengue serotype 3 (Den-3) by Virus titer reduction Assay.

The present invention provides extracts of *cissampelos pareira*, wherein the extracts have anti dengue activity.

A bioassay guided fractionation approach for the plant material leading to the identification of active extracts and fractions is provided. The process includes preparing different extracts of *cissampelos pareira*, subjecting the extracts for the bioactivity (primary screening—conventional Plaque Reduction Neutralization Test (PRNT) Assay, secondary screening—modified Plaque Reduction Neutralization Test (PRNT) Assay and tertiary screening—Virus Titer Reduction Assay). Active extracts were further subjected to fractionation by one or more of solvents and each fraction was evaluated for the bioactivity.

The one or more solvents for extraction may be, for example, water; alcohols, for example, methanol, ethanol, propanol, isopropanol or butanol; ketones, for example, acetone or methyl isobutyl ketone; esters, for example, methyl acetate or ethyl acetate; halogenated hydrocarbons, for example, chloroform, dichloromethane or ethylene dichloride; petroleum fractions, for example, hexane, petroleum ether or heptane; or mixture(s) thereof.

The one or more solvents for fractionation may be, for example, water; petroleum fractions, for example, hexane, petroleum ether or heptane; halogenated hydrocarbons, for example, chloroform, dichloromethane or ethylene dichloride; esters, for example, ethyl acetate or methyl acetate; ketones, for example, acetone or methyl isobutyl ketone; alcohols, for example, butanol; ethers, for example, diethyl ether; or mixture(s) thereof.

In another aspect of the invention, processes for the preparation of extracts from *cissampelos pareira* are provided. The processes include extracting the plant mass of *cissampelos pareira* with one or more solvents from non polar to polar range, concentrating the extract, and drying the extract, or extracting the plant mass of *cissampelos pareira* with one or more solvents from non polar to polar range, concentrating the extract, adding water and partitioning the extract with one or more solvents from non polar to polar range, and drying the extract, or extracting the plant mass of *cissampelos pareira* with one or more solvents from non polar to polar range, concentrating the extract, extracting the extract with one or more solvents from non polar to polar range, and drying the extract.

The solvents for extraction may be, for example, water; alcohols, for example, methanol, ethanol, propanol, isopropanol or butanol; ketones, for example, acetone or methyl isobutyl ketone; esters, for example, methyl acetate or ethyl acetate; halogenated hydrocarbons, for example, chloroform, dichloromethane or ethylene dichloride; petroleum fractions, for example, hexane, petroleum ether or heptane; or mixture(s) thereof.

The solvents for partitioning may be, for example, water; petroleum fractions, for example, hexane, petroleum ether or heptane; halogenated hydrocarbons, for example, chloroform, dichloromethane or ethylene dichloride; esters, for example, ethyl acetate or methyl acetate; ketones, for example, acetone or methyl isobutyl ketone; alcohols, for example, butanol; ethers, for example, diethyl ether; or mixture(s) thereof.

In another aspect of the invention, there is provided a method of treating dengue virus infection.

Pharmaceutical compositions comprising extracts of *cissampelos pareira*, along with one or more of pharmaceutically acceptable carriers, excipients or diluents are provided, which may be administered to a mammal for treatment of dengue virus infection by any route, which effectively transports the active compound to the appropriate or desired site of action such as oral, nasal, pulmonary, transdermal or parenteral (rectal, subcutaneous, intravenous, intraurethral, intramuscular or intranasal). The choice of pharmaceutical carrier, excipient or diluent can be made with regard to the intended route of administration and standard pharmaceutical practice.

The extracts of *cissampelos pareira* include (a) the extracts obtained by extraction of plant mass of *cissampelos pareira* with one or more solvents, and (b) the fractions obtained by partitioning of the extracts of step (a) with one or more solvents.

"Plant mass of *cissampelos pareira*" refers to whole plant, which includes, aerial parts, for example, fruits, flowers, seeds, leaves, branches, stem bark, stem or heartwood, and root.

While the following examples are provided to certain embodiments of the invention, these are not intended to be limiting to the scope of the invention.

Example 1: Preparation of Methanol Extract

Pulverized *cissampelos pareira* aerial parts (100 kg) were charged into the extractor. Methanol (500 liter) was added into the extractor and extraction was done at a temperature ranging from room temperature to the boiling point of the solvent for about 16 hours. The extract was filtered and stored in a container. Again, 300 liters of methanol was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The methanolic extracts were combined and concentrated to maximum under reduced pressure at low temperature. The extract was down loaded into stainless steel trays (ss) and dried in high vacuum oven at room temperature for about 16 hours to 18 hours.

Yield=6%-15%

Example 2: Preparation of (Methanol:Water: 50:50) Extract

Pulverized *cissampelos pareira* aerial parts (100 kg) were charged into the extractor. A mixture of methanol:water (250 liter:250 liter) was added into the extractor and extraction was done at temperature ranging from room temperature to the boiling point of the solvent for about 16 hours. The extract was filtered and stored in a container. Again, a mixture of methanol:water (150 liter:150 liter) was added into the extractor and extraction was done at temperature ranging from room temperature to the boiling point of the solvent for about 16 hours. The extract was filtered and stored in a container. Again, a mixture of methanol:water (150 liter:150 liter) was added into the extractor and extraction was done at temperature ranging from room temperature to the boiling point of the solvent for about 16 hours. The hydro alcoholic extracts were combined and concentrated to maximum under reduced pressure at low temperature, down loaded the extract into ss trays and dried in high vacuum oven at room temperature for about 16 hours to 18 hours.

Yield=10%-25%

Example 3: Preparation of Aqueous Extract

Pulverized *cissampelos pareira* aerial parts (100 kg) were charged into the extractor. Water (500 liter) was added into the extractor and extraction was done at temperature ranging from room temperature to the boiling point of the solvent for about 16 hours. The extract was filtered and stored in a container. Again, water (300 liter) was added into the extractor and extraction was done at temperature ranging from room temperature to the boiling point of the solvent for about 16 hours. The extract was filtered and stored in a container. Again, water (300 liter) was added into the extractor and extraction was done at temperature ranging from room temperature to the boiling point of the solvent for about 16 hours. The aqueous extracts were combined and concentrated to maximum under reduced pressure at low temperature, down loaded the extract into ss trays and dried in high vacuum oven at room temperature for about 16 hours to 18 hours.

Yield=15%-30%

Example 4: Preparation of Hexane Fraction

Pulverized *cissampelos pareira* aerial parts (100 kg) were charged into the extractor. Methanol (500 liter) was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The methanolic extracts were combined and concentrated to maximum under reduced pressure at low temperature. The extract was suspended in water (50 liter) and partitioned with hexane (40 liter). Hexane layer was separated and collected in a container. The process was repeated for three more times and combined hexane layer was dried over a drying agent. It was concentrated under reduced pressure and down loaded into ss trays and dried in high vacuum oven at room temperature for about 16 hours to 18 hours.

Yield=1.0%-3.0%

Example 5: Preparation of Chloroform Fraction

Pulverized *cissampelos pareira* aerial parts (100 kg) were charged into the extractor. Methanol (500 liter) was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The methanolic extracts were combined and concentrated to maximum under reduced pressure at low temperature. The extract was suspended in water (50 liter) and partitioned with hexane (40 liter). The hexane layer was separated and collected in a container. The process was repeated for three more times and combined hexane layer was dried over a drying agent and concentrated. The remaining aqueous layer was partitioned with chloroform (40 liter) and chloroform layer was separated and collected in a container. The process was repeated for three more times and the combined chloroform layer was passed through a drying agent. The chloroform layer was concentrated under reduced pressure and down loaded into ss trays and dried in high vacuum oven at room temperature for about 16 to 18 hours.

Yield=0.20%-1.0%

Example 6: Preparation of Dichloromethane Fraction

Pulverized *cissampelos pareira* aerial parts (100 kg) were charged into the extractor. Methanol (500 liter) was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The methanolic extracts were combined and concentrated to maximum under reduced pressure at low temperature. The extract was suspended in water (50 liter) and partitioned with hexane (40 liter) and hexane layer was separated and collected in a container. The process was repeated for three more times and combined hexane layer was dried over a drying agent and concentrated. The aqueous layer was partitioned with dichloromethane (40 liter) and dichloromethane layer was separated and collected in a container. The process was repeated for three more times and the combined dichloromethane layer was passed through a drying agent. The dichloromethane layer was concentrated under reduced pressure and down loaded into ss trays and dried in high vacuum oven at room temperature for about 16 hours to 18 hours.

Yield=0.22%-1.2%

Example 7: Preparation of Dichloromethane Fraction

Pulverized *cissampelos pareira* aerial parts (100 kg) were charged into the extractor. Methanol (500 liter) was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The methanolic extracts were combined and concentrated to maximum under reduced pressure at low temperature. The extract was suspended in water (50 liter) and partitioned with dichloromethane (40 liter) and dichloromethane layer was separated and collected in a container. The process was repeated for three more times and the combined dichloromethane layer was passed through a drying agent. The dichloromethane layer was concentrated under reduced pressure and down loaded into ss trays and dried in high vacuum oven at room temperature for about 16 hours to 18 hours.

Yield=1.0%-1.75%

Example 8: Preparation of Butanol Fraction

Pulverized *cissampelos pareira* aerial parts (100 kg) were charged into the extractor. Methanol (500 liter) was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The methanolic extracts were combined and concentrated to maximum under reduced pressure at low temperature. The extract was suspended in water (50 liter) and partitioned with hexane (40 liter) and hexane layer was separated and collected in a container. The process was repeated for three more times and the combined hexane layer was dried over a drying agent and concentrated. Aqueous layer was partitioned with chloroform (40 liter) and chloroform layer was separated and collected in a container. The process was repeated for three more times and the combined chloroform layer was passed through a drying agent and concentrated. Aqueous layer was partitioned with butanol (40 liter) and the butanol layer was separated and collected in a container. The process was repeated for three more times and the combined butanol layer was dried over a drying agent. The butanol layer was concentrated under reduced pressure and down loaded into ss trays and dried in high vacuum oven at room temperature for about 16 hours to 18 hours.

Yield=2.0%-4.5%

Example 9: Preparation of Aqueous Fraction

Pulverized *cissampelos pareira* aerial parts (100 kg) were charged into the extractor. Methanol (500 liter) was added into the extractor and extraction was done at temperature ranging from room temperature to the boiling point of the solvent for about 16 hours. The extract was filtered and stored in a container. Again, 200 liter of methanol was added into the extractor and extraction was done at temperature ranging from room temperature to the boiling point of the solvent for about 16 hours. The extract was filtered and stored in a container. Again, 200 liter of methanol was added into the extractor and extraction was done at temperature ranging from room temperature to the boiling point of the solvent for about 16 hours. The methanolic extracts were combined and concentrated to maximum under reduced pressure at low temperature. The extract was suspended in water (50 liter) and partitioned with hexane (40 liter) and hexane layer was separated and collected in a container. The process was repeated for three more times and combined hexane layer was dried over a drying agent and concentrated. The aqueous layer was partitioned with chloroform (40 liter) and the chloroform layer was separated and collected in a container. The process was repeated for three more times and the combined chloroform layer was passed through a drying agent and concentrated. The aqueous layer was partitioned with butanol (40 liter) and the butanol layer was separated and collected in a container. The process was repeated for three more times and the combined butanol layer was dried over a drying agent and concentrated. The exhausted aqueous layer was concentrated under reduced pressure and down loaded into ss trays and dried in high vacuum oven at room temperature for about 16 hours to 18 hours.

Yield=2.5%-6.0%

Example 10: Preparation of Ethyl Acetate Fraction

Pulverized *cissampelos pareira* aerial parts (100 kg) were charged into the extractor. Methanol (500 liter) was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The methanolic extracts were combined and concentrated to maximum under reduced pressure at low temperature. The extract was suspended in water (50 liter) and partitioned with ethyl acetate (40 liter) and the ethyl acetate layer was separated and collected in a container. The process was repeated for three more times and the combined ethyl acetate layer was dried over a drying agent. Ethyl acetate layer was concentrated under reduced pressure and down loaded into ss trays and dried in high vacuum oven at room temperature for about 16 hours to 18 hours.

Yield=2.0%-4.0%

Example 11: Preparation of Acetone Fraction

Pulverized *cissampelos pareira* aerial parts (100 kg) were charged into the extractor. Methanol (500 liter) was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The extract was filtered and stored in a container. Again, 300 liter of methanol was added into the extractor and extraction was done at temperature ranging from room temperature to the boiling point of the solvent for about 16 hours. The methanolic extracts were combined and concentrated to maximum under reduced pressure at low temperature. The extract was extracted with acetone (50 liter) at temperature ranging from room temperature to the boiling point of the solvent for about 2 hours to 3 hours. The extract was filtered and stored in a container. The process was repeated for three more times. The extract was down loaded into ss trays and dried in high vacuum oven at room temperature for about 16 hours to 18 hours.
Yield=2.0%-3.5%

Example 12: Biological Activity (i) Primary Screening—Conventional Plaque Reduction Neutralization Test (PRNT) Assay The antiviral activity of extracts was assayed using the PRNT assay (Khanam et. al., Am. J. Trop. Med. Hyg., 74(2) p. 266-277 (2006), LLCMK2 cells (monkey kidney cell line) in 24 well format were seeded at a concentration of $1\times10^5$/well. Infection was done with approximately 50 plaque forming units (PFU) of dengue virus (DENV) (all four serotypes DENV-1, DENV-2, DENV-3, and DENV-4) at a multiplicity of infection (MOI) of 1. Viruses were separately pre-incubated with an equal volume of extracts in the range of 100-0.33 mcg/ml. After overnight preincubation at 4° C., the viruses/extracts were diluted to a final volume of 200 µL with Dulbecco's Modified Eagles Medium (DMEM) plus 2% heat inactivated Fetal calf serum (ΔFCS) and used to infect a single well of 24-well plate. Each dilution was assayed in duplicate wells and the virus/extract preincubation mixture was prepared as a master mixture sufficient for two wells. After adsorption for two hours, the inoculum was aspirated off and the cells were overlaid with 1.25% methylcellulose in DMEM plus 6% ΔFCS (1 mL/well). Appropriate controls were set up in parallel with negative control (mock—not infected) wells receiving 200 µL of DMEM plus 2% ΔFCS and positive control wells receiving (DEN-1, 2, 3 and 4 viruses separately), pre-incubated with DMEM plus 2% AFCS, instead of extracts. Plates were incubated at 37° C. in a humidified 5% $CO_2$ incubator. On day 6 post-infection, the cells were fixed with 1 mL of 4% formaldehyde solution at room temperature for two hours. Wells were washed with tap water and then stained with 1:40 diluted stock of 2% crystal violet solution in 20% ethanol for 30 minutes. Plaques revealed after staining were counted and the extract dilution resulting in 50% reduction in plaque count (with reference to the number of plaques generated by the virus in the absence of extract), was expressed as $PRNT_{50}$ titer.

Methanolic extract showed activity against all the four serotypes of Dengue in conventional assay with $PRNT_{50}$ values in the range of 1.2-11.1 mcg/ml. $PRNT_{50}$ values of hydroalcoholic and aqueous extracts in conventional assay against all the serotypes were >100 mcg/ml.

(ii) Secondary Screening—Modified Plaque Reduction Neutralization Test (PRNT) Assay LLCMK2 cells in 24 well format were seeded at a concentration of $1\times10^5$/well. Seeded cells were infected with approximately 50 µl of virus with 50 (1×) plaque forming units (PFU) of all 4 serotypes at a MOI of 1. After adsorption for two hours at 37° C. and 5% $CO_2$, the inoculum was aspirated. Wells were washed with phosphate buffered saline (PBS) and infected cells were exposed to different concentrations of extracts (200-0.82 mcg/ml) for a period of 24 hours. After 24 hours of incubation at 37° C. and 5% $CO_2$, extract was aspirated out and the cells were overlaid with 1% methylcellulose in DMEM plus 6% ΔFCS (1 ml/well). Each dilution was assayed in duplicate wells. Plates were incubated at 37° C. in a humidified 5% $CO_2$ incubator for 6 days. On day 6 post-infection, the overlay was gently decanted and the cells were fixed with 1 mL of 4% formaldehyde solution at room temperature for one hour. Wells were washed with tap water and then stained with 1:40 diluted stock of 2% crystal violet solution in 20% ethanol for 30 minutes. Plaques revealed after staining were counted and the extract dilution resulting in 50% reduction in plaque count (with reference to the number of plaques generated by the virus in the absence of extract), was expressed as the $PRNT_{50}$ titer.

Methanolic extract showed $PRNT_{50}$ values in the range of 78-125 mcg/ml in modified assay against all the four serotypes. However, hydroalcoholic and aqueous extracts were inactive up to 200 mcg/ml.

(iii) Tertiary Screening—Virus Titer Reduction Assay

Virus Titer Reduction Assay was performed by following Puig-Basagoiti et al., Antimic. Agents and Chemotherapy, 50(4) p. 1320-1329 (2006). Vero cells in 24 well format were seeded at a concentration of $1\times10^5$/well. Seeded cells were infected with approximately 50 µl of virus with 50 (1×) plaque forming units (PFU) of all 4 serotypes at a MOI of 1. After adsorption for two hours at 37° C. and 5% $CO_2$, the inoculum was aspirated. Wells were washed with PBS and infected cells were exposed to growth medium (DMEM plus 2% ΔFCS) with different concentrations of extracts (200-0.82 mcg/ml) along with negative control (mock—not infected) wells receiving DMEM plus 2% AFCS and positive control wells receiving DEN-3 viruses, for a period of 9 days. 20 µl of supernatant sample was withdrawn at different days intervals, i.e., 0, 3, 6, 9 days and frozen down till further processing.

The aliquoted samples were serially diluted in DMEM plus 2% ΔFCS medium prior to addition to the wells containing confluent cells (in duplicate or triplicate). The viruses were allowed to adsorb for two hours, followed by washing with phosphate-buffered saline. After adsorption for two hours, the inoculum was aspirated off and the cells were overlaid with 1.25% methylcellulose in DMEM plus 6% ΔFCS (1 mL/well). The plates were incubated at 37° C. in a humidified 5% $CO_2$ incubator for 6 days. On day 6 post-infection, the overlay was gently decanted and the cells were fixed with 1 mL of 4% formaldehyde solution at room temperature for one hour. Wells were washed with tap water and then stained with 1:40 diluted stock of 2% crystal violet solution in 20% ethanol for 30 minutes.

Plaques revealed after staining were counted and log reduction in plaque titer at different time points vs different tested concentrations were calculated as compared to virus control.

Kill kinetic profile of methanolic extract indicated a 2 log reduction on day 3 at 66.66 mcg/ml against Den-3 serotype. On day 6, at 2.46 and 7.4 mcg/ml concentration of extract, viral load was reduced by 1-1.5 log.

(iv) Cytotoxicity Assays

Cytotoxicity of methanolic extract was assessed by incubating HEpG-2 cells (Human liver hepatoma cell line) with a six point dilution of extract (concentration range of 200 mcg/ml-0.82 mcg/ml) in culture medium RPMI (Roswell Park Memorial Institute) 2% ΔFCS in 96-well plates for 3 days, corresponding to the incubation period of cells with extracts in the primary and secondary screens. After 72 hours, cell viability was measured by cellular metabolism of MTT (3-[4,5-dimethylthiazol-2-yl]-2,5-diphenyltetrazolium bromide) Narkland W. et al., Antimic. Agents and Chemotherapy, 44(4) p. 859-866 (2000)). Growth index (GI) 50 was found to be 90 mcg/ml.

We claim:

1. A method of treating dengue virus infection by reducing the virus titer, wherein the method comprises administering to a patient in need thereof a therapeutically effective amount of a methanolic extract of *cissampelos pareira*, thereby reducing the virus titer.

2. The method of claim 1, wherein the extract of *cissampelos pareira* is a pharmaceutical composition comprising the extract of *cissampelos pareira* along with one or more of pharmaceutically acceptable carriers, excipients or diluents.

* * * * *